United States Patent [19]

Queiroz et al.

[11] Patent Number: 5,399,786
[45] Date of Patent: Mar. 21, 1995

[54] PREPARATION PROCESS OF TERT-BUTYLPHENOLS

[75] Inventors: Antonio U. B. Queiroz, Centro Campinas; Lumi T. Aikawa, deceased, late of Campinas, both of Brazil, by Sachio Aikawa, executor

[73] Assignee: Rhodia S/A, Sao Paulo, Brazil

[21] Appl. No.: 91,072

[22] Filed: Jul. 13, 1993

[30] Foreign Application Priority Data

Jul. 22, 1992 [BR] Brazil .................... 9202890

[51] Int. Cl.⁶ ............................................ C07C 37/16
[52] U.S. Cl. ................. 568/785; 568/780; 568/783; 568/784
[58] Field of Search ............... 568/784, 785, 788, 789, 568/783, 780

[56] References Cited

U.S. PATENT DOCUMENTS 4,359,591 11/1982 Fremery et al. ................ 568/804
4,370,506 1/1983 Ancillotti et al. ............... 568/788

FOREIGN PATENT DOCUMENTS 51901 9/1970 Australia ................ 568/788

2081710 2/1982 United Kingdom .

OTHER PUBLICATIONS

Chemical Abstracts, vol. 96, No. 17, 26 Apr. 1982, Columbus, Ohio, US; abstract No. 142445, *abrégé* & BR-A-8 002 607 (Rhodia S.A.).

*Primary Examiner*—Werren B. Lone
*Attorney, Agent, or Firm*—Ladas & Parry

[57] ABSTRACT

The present invention has as purpose a process for the manufacture of tert-butylphenols, mainly of tertbutyl-4-phenols from a phenol and an alkyltert-butylether. The improvement consists in separating in at least two steps, the reaction of phenol alkylation and transalkylation-/isomerization of undesirable alkyltert-butylphenols, enabling the flexibilization of the type and quality of end product, and easily adapt to the demands of the market, plus the fact that the total yield improved as well as this improvement has good industrial hygiene properties.

Tert-butylphenols are useful intermediate products is the manufacture of phenolic resins or antioxydizing agents for rubber and for several plastic substances.

24 Claims, 2 Drawing Sheets

PREPARATION PROCESS OF TERT-BUTYLPHENOLS

BACKGROUND OF THE INVENTION

The present invention has as object a process for the preparation of tert-buthylphenols, mainly tert-butyl-4-phenols, starting from phenols and an alkyltert-buthylether.

The tert-butylphenols are useful intermediates in the manufacturing of phenolic resins or antioxidants for rubber and for different plastic materials.

Such compounds are traditionally obtained by alkylation of a phenol by means of isobutilene in the presence of an acid catalyst (according to Kirk Othmer—"Enc. of Chem. Techn." 3rd edition, vol. 4, page 364).

An essential problem encountered in the manufacturing at industrial proportions lays in the need of working with practically pure isobutylene.

As a matter of fact, isobutylene is one of the components of C4 fractions resulting from the vapour cracking of satured hydrocarbons, originated from natural gas or from petroleum, or from the catalytic cracking of the petroleum fraction at refining operations used to produce gasolines. In general, such C4 fractions contain different proportions of isobutylene, butenes and traces of butadiene. Isobutylene can not be easily isolated from such fractions for it is very difficult to separate it, mainly from 1-butene. For such reason, when one wants to obtain a relatively pure isobutylene, one should employ very elaborate separation techniques (selective extraction or absorption) according to Kirk Othmer—'-'Enc. of Chem. Tech." 3rd edition, vol. 4, pages 346 and next).

Isobutylene may be equally produced by isobutanol dehydration. However, in this event one also obtains an impure product which, when used for alkylating phenols, leads to the formation of phenol by-products, such as derivatives which have a secundary butyl substitute wich are difficult to separate from the compounds searched for which contain a tert-bytil substitute.

It was proposed to introduce methanol in fraction C4, which would come from any one of the cracking operations listed above, to convert isobutylene in situ in methyltert-butylether. In this C4 fraction, eventually previously free of butadiene trances, only isobutilene reacts with methanol. Methyltert-butylether is then easily separated from C4, mainly from butenes (1 and 2). Besides using this ether as an additive for gasolines (unleaded fuel) to incresse their octane level, one may also crack it in methanol and isobutylene. Therefore, methyltert-butylether is being increasingly considered as being an intermediate of choice in the preparation of pure isobutylene which one needs for the preparation of tert-butylphenols (according toi Chem and Eng. News, from Jun. 25, 1979, page 35-36).

Analysing the state of the art in the technique, in 1983 we found a patent CS 79-1487, which claims the alkylation of phenols and/or alkylphenols through the reaction of said phenols and/or alkylphenols with a Me 3 COR (where R=H, Me, ChMeEt.) As example, they mention the reaction of phenol with Me3COH in an inert N2 atmosphere (as they use isobutanol, an inert N2 atmosphere is needed to avoid the formation of impurities, besides those impurities which are a result of the reaction itself). The catalyst used could be necessarily chosen among strong inorganic acids, acid cations exchangers and/or phosphor oxides (polyphosphoric acids).

In 1985, we found a paper named "HIGHLY SELECTIVE MONO-TERT-BUTYLATION OF AROMATIC COMPOUNDS" by G. Sartori, F. Bigi, G. Casiraghi, G. Casnati, L. Chiesi and A. Arduini, published by Chem. Ind. (London) (22) 762-3. In this paper are published the reactions of PhR (R=H, Me, MeO, Cl) with Me3COMe or isobutene in the presence of ZrO4 yielding 85% of 4-Me3CC6H4R. They studied the efficiency of ZrO4 as acid catalyst and, as we will show below, according to the invention of the Petitioner, we obtained tert-butylphenols with catalysts known by those skilled in the art, but with high yield and degree of purity of the high and controlled end product.

Patent DD 87-311221 (Dec. 24, 1987) deals with a process for the preparation of mono, bi-tri-tert-alkylated benzene derivatives using n-alkyltert-alkylethers, and the process temperature, mainly the reaction temperature, in the example 288° C., is much higher that the temperatures used in the Petitioner's process. Those skilled in the art know that equimolar amounts of phenol and acid unfailingly generate corrosion problems due to high temperature, thus demanding a special material for the reactor. There would be also a higher energy consumption, and during the purification process of the final process is made washing with water and later recrystallization which doubtlessly yields a less pure product than thoses processes which use distillation.

In 1980, the Petitioner filed an invention priviledge request PI 8002607 on a process which uses directly alkyltert-butylethers for the preparation of tert-butyl-phenols. According to this basic invention of the Petitioner, a reaction occurred between alkyltert-butylether with phenol at a temperature ranging between 95° and 180° C. and pressure around athmospheric pressure, in the presence of an acid catalyst such as a Lewis acid, a strong acid with protons or cationic exchange resin of the sulphonic type. The molar ratio alkyltert-butylether/phenol could range from 0,1:1 to 2:1. The phenol alkylation reaction and also transalkylation/isomerization reactions of undesired tert-butylphenols, took place in one single step, i.e. concurrently.

Until 1989, the Petitioner was manufacturing the product paratert-butylphenol, however with control problems in the distillation of end product phase (the samples for quality control were obtained manually by the operators, exposing them constantly to an unhealthy environment), was forced to reevaluate their process, aiming its optimization in order to eliminate industrial hygiene problems, improve the quality of end product, maintaining or even reducing the cost of such process.

The Petitioner developed a new process which solves the problem of industrial hygiene, improves the quality of end product, increasing its degree of purity and, most importantly improved the yield of the process, without any increases in power consumption, therefore not increasing costs.

The Petioner was able to increase the yield of the Basic Process (according to PI 8002607) from 78,9% to for instance 94,8%.

In terms of global yield of the process, we may state that it increased from 88.7% (basic process) to 94.8% for reacted phenol and from 80.5% (basic process) to 89.0% for reacted alkyltert-butylether.

Another advantage of such process is the possibility of a total operational flexibility to adjust the quality of paratert-butylphenol thereafter called PTBF, with no yield losses (increasing the value of intermediate product). Therefore, for instance, the Petitioner markets two types of PTFB with different specifications. One technical degree PTFB, which corresponds, for instance to the specifications:

| | |
|---|---|
| Content of PTFB | at least 98.5% |
| Crystallization point | 97.5° C. |
| APHA Color, melted | 100 maximum |
| Content of dialkylphenols | below .8% |

And another type called polycarbonate PTBF which obeys the following specifications:

| | |
|---|---|
| Content of PTBF | at least 99.5% |
| Crystallization point | 97.5° C. |
| APHA Color, melted | 90 maximum |
| Orthotert-butylphenol content | below .05% |
| Dialkylphenol content | below .055% |
| Phenol content | below .1% |

As we can see the PTFB polycarbonate content would be a product with a higher degree of purity and nobler uses than technical PTFB.

One of the advantages of this process, is that depending of the purification by distillation of the end product, or better, depending of the cuts of fractions of distillation columns, one may obtain as final product, PTBF technical degree of PTBF polycarbonate degree. According to this process, it is easy to render flexible the type of end product, according to market demands.

SUMMARY OF THE INVENTION

The present invention has as purpose a novel process for the obtention of tert-butylphenols, characterized by the following steps:

a) Alkylation: reacting continuosly or intermitently in a fluid, stirred or fluidized bed an alkytert-butylether whose alkyl group contains from 1 to 6 carbon atoms with a phenol at a temperature ranging from 60° to 130° C. and pressure between atmospheric pressure and 5 kg/cm$^2$, in the presence of an acid catalyst, of the strong acid type with protons or Lewis acid, being the molar ratio alkyltert-butylether:phenol used ranging between 0.1:1 and 2:1.

b) Distillation of lights: the product so obtained in step a, passes through a distillation column continuously or intermittently, with a temperature ranging from top to bottom between −15° and 120° C. and pressure between 10 mm Hg and around 5 kg.cm$^2$.

c) Isomerization/transalkylation: the product received at the bottom of step b is routed for a reactor, continuously or intermittently, in a fixed, stirring bes reactor, in the presence of a catalyst of the type used in step a, whose temperature may range approximately between 90° and 250° C. and pressure between around 10 mm Hg and 5 kg/cm$^2$.

d) Neutralization: the product obtained at the end of the previous step and follows to a neutralization step with alkalis or resins known to those skilled in the art at a temperature ranging between 40° C. and 250° C. approximately and a pressure ranging between the atmospheric pressure and around 5 kg/cm$^2$.

s) Separation of lights/tert-butylphenol: another distillation step follows at a temperature variyng from top to bottom between around 80° C. and around 200° C. and pressure ranging between 10 mm Hg and 200 mm Hg, this being obtained products at the top of the column which may be recycled for the alkylation reactor;

f) Rectification: the product obtained at the base of the column in the previous step follows to a rectification step, for the separation of the desired end product, by means of a distillation, where at the top of the column is produced the desired tert-butylphenol, working at a temperature ranging from the base to top from about 115° C. tp about 200° C. and pressure 10 to 20 mm Hg;

g) Optionally concentration of heavies: the product obtained at the base of the column in the rectification step of f step, optionally passes through an evaporator, on top of which are released bi-tert-butylphenols, which are recycled for step a, or alkylation step.

One may carry out steps a, b and c in one single reactor with intermitent stirring, reacting in a first step an alkyltert-butylether, whose alkyl group contains 1 to 6 carbon atoms with a phenol at a temperature ranging from around 60° to around 130° C. and pressure ranging from atmospheric pressure to 5 kg/cm$^2$, in the presence of a strong acid catalyst, protonated or a Lewis acid, being the molar ratio tert-butylphenol:phenol used ranging between 0.1:1 and 2:1. The distillation of the alcohol (and lights in the reaction) may take place simultaneously in this step, or after the alkylation phase during the passage to isomerization/transalkylation phase attained with the increase of temperature, being this step higher or equal to 90° C. or equal to 250° C. and pressure ranging between approximately atmospheric pressure and 5 kg/cm$^2$.

Also another alternative system would be non recycling the product obtained at the top of the separation column of lights/tert-butylphenols, before rectification step, directly to the beginning of the process (alkylation step), as was already mentioned, but send it for an additional step comprising distillation and a concurrent or consecutive translakylation/isomerization step. The isomerization/translakylation reactor may be under stirring or fixed bed at a temperature ranging from 90° to around 250° C. and pressure ranging between 10 mm Hg and 5 kg/cm$^2$ and the product from such reaction would be recycled, in both cases, to the first step or alkylation step.

Also de bitert-butylphenols obtained at the top of the heavies concentrator from step "g", recycled to step "a" or alkylation step, could also be recycled for an additional isomerization/translakylation step.

The inventions deals with a novel process for the obtention of tert-butylphenols, with increased yield, with relationship to the consumption of alkyltert-butylether, for instead of processing alkylation and isomerization/translalkylation steps in one single step, as in basic process, these steps are processed separately in different steps, improving the quality of the end product and increasing the value of intermediate products.

DETAILED DESCRIPTION OF THE INVENTION

Figure 1:
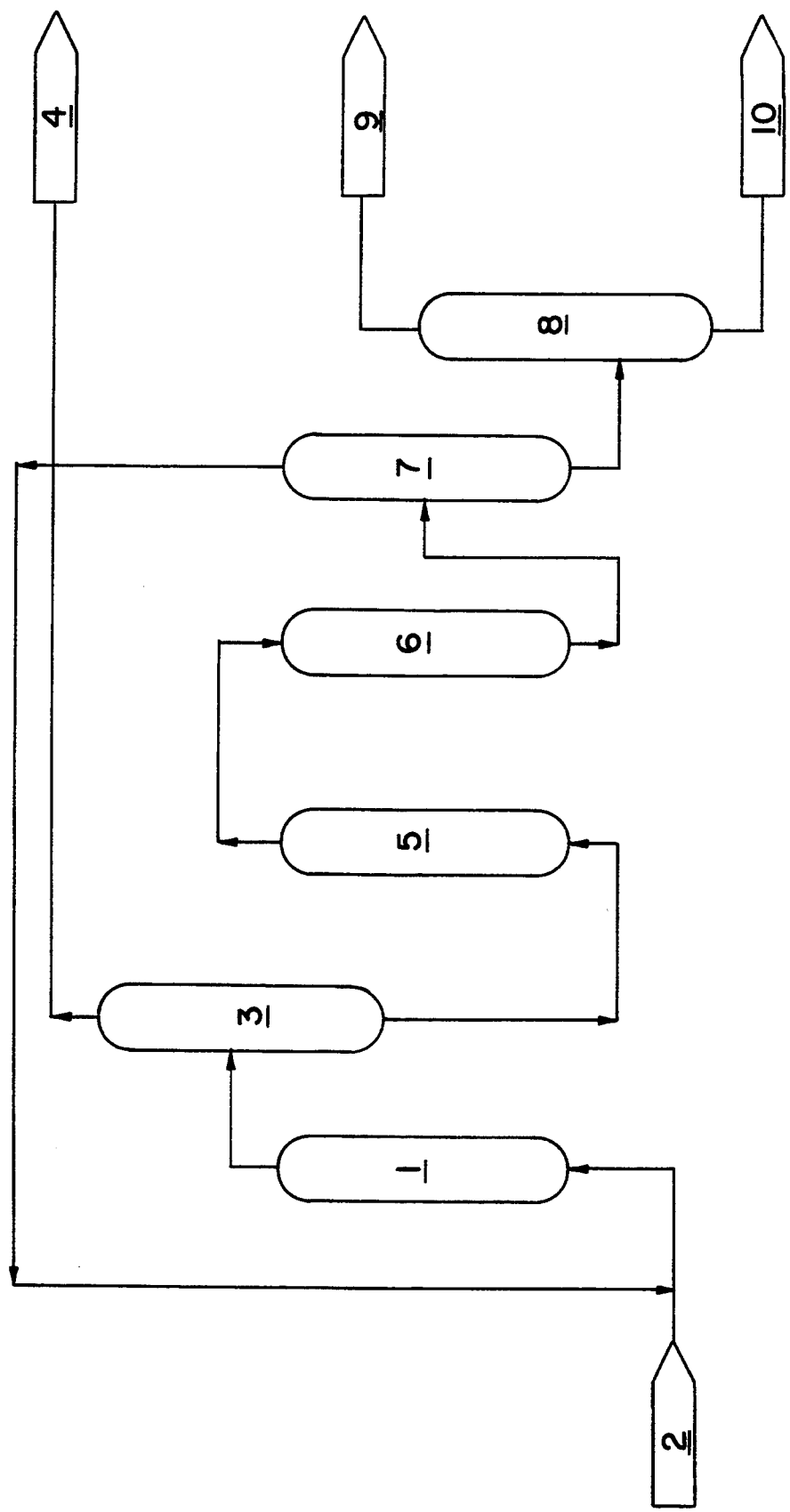
Figure 2:
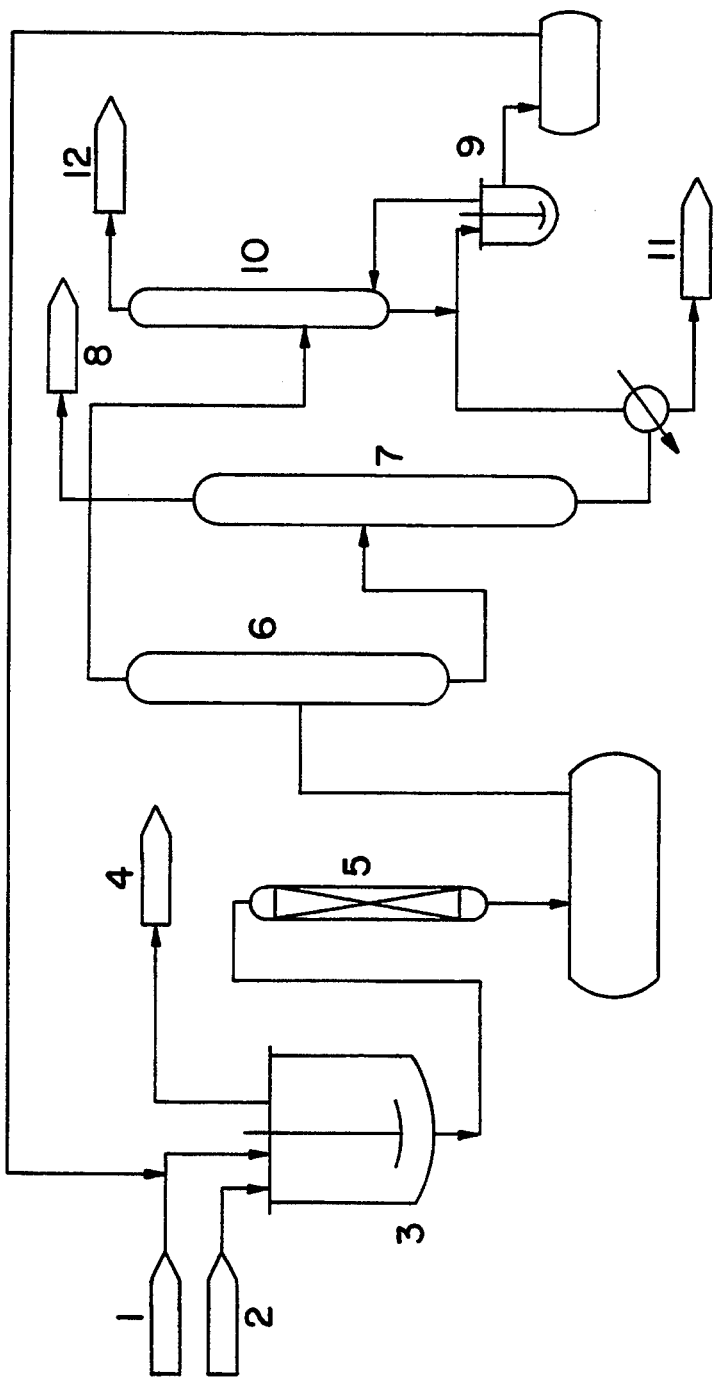

The first step of the new process, or step "a", corresponds to an alkylation step, where there is a reaction of alkyltert-butylether, whose alkyl group contains from 1 to 6 Carbon atoms with phenol, with the formation of tert-butylphenol and alcohol as shown in the formula (I):

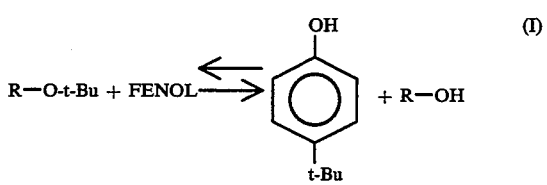

The alkyltert-butylether has an alkyl group with at most 6 Carbon atoms. Phenol is chosen in the group made by phenol, methyl-2-phenol (o-cresol), di-methyl-2,3-phenol, dimethyl-2,5 phenol and dimethyl-2,6 phenol. This step may take place continuously or intermitently, in a fixed, stirred or fluidized bed reactor.

According to the present invention, one puts into contact an alkyltert-butylether and one of the above mentioned phenols, in such conditions that at least one part of the reagents is in liquid state. Even that, as an hypothesis, one may operate under a pressure below or above atmospheric pressure and preferably between 1 and 5 kg/cm². It is comfortable to work at atmospheric pressure.

The temperature of the reaction usually ranges between around 60° and around 130° C., preferably between approximately 70° and 110° C.

The reagents ratio may vary between broad limits. As one aims more specifically the preparation of phenols containing just one tert-butyl substitutes, the stechiometry of the reaction implies in the presence of one mol of alkyltert-butylether per mol of the phenol employed. However, one may operate with a slight excess of ether, i.e., with a molar ratio alkyltert-butylether/phenol which may reach, for instance 2, or with an excess of phenol, and then the ratio tert-butylether/phenol may be 0,1.

The reaction is conducted in presence of an efficient amount of protonated strong acid and/or a Lewis acid, known by those skilled in the art. As exemples of protonated acids, susceptible of being used in the scenario of the present process may be mentioned: sulphuric acid, phosphoric acid, arylsulphonic acids (mainly p-toluenesulphonic acid) and cationic exchange resins of the sulphonic type. As examples of Lewis acids susceptible of being convenient to carry out the present invention may be mentioned aluminum trichloride and boron trifluoride. In the process now being described, it is envisaged preferably the use of protonated strong acids, and more especifically cationic exchange resins of the sulphonic type, all known by those skilled in the art.

The reaction also may be conducted in the presence of a cationic exchange resin with macro recticular structure of the sulphonic type based on a styrene-divinylbenzene copolymer. This type of resin is marketed, for instance, by one of the manufacturers under the name AMBERLYST 15. For more informations on this type of resins, please report to the paper by R. KUNIN et al., "I and E.C. Product Research and Development" vol. 1, No. 2 from June 1962, pages 140–144. The amount of resin usually ranges between 0,05 and 1 part per 1 part of phenol employed in the reaction, even if lower or higher amounts may be used. Good results are obtained with 0.2 to 0.8 parts of resin per part of phenol used in the reaction. These resins are part of the state of the art technique.

As was already mentioned, to obtain tert-butylphenol, reacting and ether with phenol, one obtains as product of the reaction, the desired tert-butylphenol and an alcohol. Thus, for instance, reacting methyltert-butylesther, hereinafter called MTBE with phenol, one would mainly obtain para-tert-butylphenol, hereinafter called PTFB and methanol as products of the reaction. As secondary products, we would have the formation of anisole and methanol, considered as lights in the reaction. The orthotert-butylphenol (OTBF) and para-tert-butylanisolee (PTBA) are considered as intermediate. As heavies of the reaction we could mention ditertbutylphenols as, for instance, 2,4-ditert-butyl phenol (2,4 di-TBF) and the 2,6-ditert-butylphenol (2,6 di-TBF). The alcohol, in this example the methanol, should be eliminated, for in the presence of alcohol, the methylation of PTFB may take place, forming paratert-butylanisole (PTBA) and also, the methylation of phenol in anisole, as shown by equations (I) and (III)

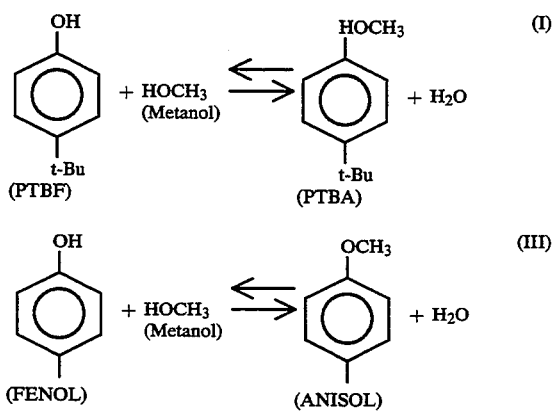

Therefore, as a consequence it is necessary to remove lights which contain methanol, or non reacted alcohol from the reaction environment. Step b has as one of its goals avoid these reactions. It may take place continuously or intermitent and corresponds to a distillation step of the alcohol, for instance methanol formed in the first alkylation step.

The temperature in this distillation step ranges between −15° and 120° C. and the pressure is encompassed in the approximate range of 10 mm Hg and 5 kg/cm². Thus, one is able to separate lights from the reaction environment (which will be burned or recovered) as for instance the alcohol formed, non reacted alkyltert-butylether, steam, etc. which leave the top of the distillation column and the product from the base which corresponds mainly to non reacted alkylphenols and phenol.

In step c, the product from the bottom of the column from the previous step, the tert-butylphenols different from those desired ones, are transalkylated or submitted to isomerization into the desired tert-butylphenol at a temperature ranging from 90° and around 250° C., preferably between 100° and 160° C. approximately and pressure encompassed between less than 10 mm Hg and not over 5 kg.cm². The same media from the alkylation step is used. In this conditions, one is able to attain, for instance, the isomerization of OTBF in PTBF as seen in formula IV:

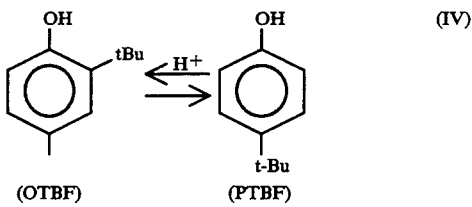

Translakylation of PTBA in PTBF, through its reaction with non reacted phenol, may represented by formula (V):

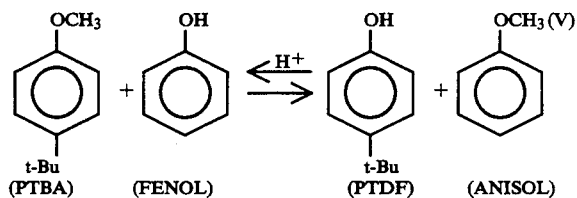

Transalkylation of PTBA is favored when there is an excess of phenol and absence of PTBF. Anisole is distilled together with the lights and proceeds to be burned. Example No. 1 explains well this displacement of balance. This step may take place continuously or intermitently in a fixed, stirred or fluidized bed reactor.

One of the most important points of this invention is the fact that alkylation and isomerization and transalkylation steps take place separately, favoring the total yield of the process and increasing the value of the intermediate products in the alkylaton step. Even though, one may optionally substitute the three previous steps a, b and c for one single step, working with a reactor with simultaneous stirring and distillation. Reagents, i.e., an alkyltert-butylether, whose alkyl group has from one to six carbon atoms with a phenol, would be placed into the reactor, the temperaturre in a first step would range between 60° and at most 130° C. (preferably between 60° and 110° C.) ahd pressure ranging between atmospheric pressure and 5 kg/cm$^2$, in the presence of an acid catalyst of the protonated strong acid or Lewis acid, being the molar ratio alkyltert-butylether:fenol used between 0.1:1 and 2:1. At this first step, the alkylation reaction would take place.

In a second step, temperature would rise to a range between 90° and 250° C., preferably between 100° and 160° C. and pressure would remain approximately between atmospheric pressure and 5 kg/cm$^2$, preferably around atmospheric pressure.

During this second step, transalkylation reaction would take place such as paratert-butylanisole (PTBA) and ditert-butylphenol (di-TBF), originating PTBF, through its reaction with non reacted phenol and isomerization as for instance from ortotert-butylphenol into paratert-butylphenol. During the first and/or second step we would have the escape of lights such as alcohol (for instance methanol) formed in the reaction, non reacted alkyltert-butylether, steam, etc.

Next step would be the neutralization of the acid mass obtained up to that moment, this to avoid the possible medium or long corrosion of the equipment used in the manufacturing process of tert-butylphenol, or to avoid the manufacturing of undesirable products due to balance shifts which take place in acid environemnt, as shown in formula (IV). We can revert the balance of the reaction favoring the formulation of OTBF). The neutralizing agent may be chosen among those known by those skilled in the art, but this will depend more specifically from the catalyst used in the reaction. This step takes place at a temperature ranging between approximately 40° and maximum of 250° C. (preferably between 60° and around 150° C.) and pressure ranging between atmospheric pressure and approximately 5 kg/cm$^2$ (preferably around atmospheric pressure).

Next comes a distillation step, corresponding to the beginning of purification of tert-butylphenol, through the separation of ligths/tert-butylphenol, taking place at a temperature from top to bottom equal or higher than 80° C. and lower or equal to 200° C. and pressure ranging between around 10 mm Hg and 200 mm Hg. The product which escapes from the top of the distillation column may receive three different and alternative destinations. The first would be recycle it for the alkylation step. The second alternative would be submit it to an additional reaction step of transalkylation/isomerization in a reactor with distillation column which would allow the concurrent withdrawal of the light which had remained in the reactional mass (as for instance alcohol, water, etc.) and, for instance, anisole formed in this step. The temperature of the reactor may range between approximately 90° and approximately 250° C. (preferably between 100° and 160° C.) and pressure being situated in the approximate interval of 100 mmHg and 5 kg/cm$^2$. The product obtained at this additional step would be recycled for the initial alkylation step. The third alternative would be similar to the first one in what concerns temperature and pressure conditions, i.e., temperature ranging between approximately 90° and 250° C., preferably between 100° and 160° C. and pressure chosen between around 10 mmHg and 5 kg/cm$^2$. The difference is that first a distillation step of the lights would take place and then would follow the additional step for transalkylation/isomerization in a fixed or stirred bed reactor, being the product obtained recycled in the same way, i.e., for the alkylation step.

In the desired product rectification step, one starts with the product from the base of the previous step, basically made up by the desired tert-butylphenol and heavies formed mainly by the di-tert-butylphenols. Rectification is carried out at a temperature form top to base, lower or equal to 115° C. and higher or equal to 200° C., while pressure may be ranging between the interval of at least 10 and at most 200 mmHg. At the top of the column we would come out the desired tert-butylphenol and at the base heavies containing dialkylphenols. These may or may not be routed for a last step of concentration of heavies, in which heavies plus di-tert-butylphenols would pass through an evaporator, from the top of which would come out ditert-butylphenols which would be recycled for the alkylation step or for the additional step of isomerization/transalkylation in a reactor with previous or concurrent distillation (after the lights/tert-butylphenol separation step). The heavies which exit from the base are directed to be burned. Di-tert-butylphenols reacted in acid environment under heating with non reacted phenol forming the desired tert-butylphenol. Only as example, if the tert-butylphenol is paratert-butylphenol (PTBF), the reaction shall take place between the two di-tert-butylphenols, usually formed, the 2,4-ditert-butylphenol (2,4 di-TBF) and 2,6-ditert-butylphenol (2,6 di-TBF) with phenol in excess, as indicated in the equations (VI) and (VII) below:

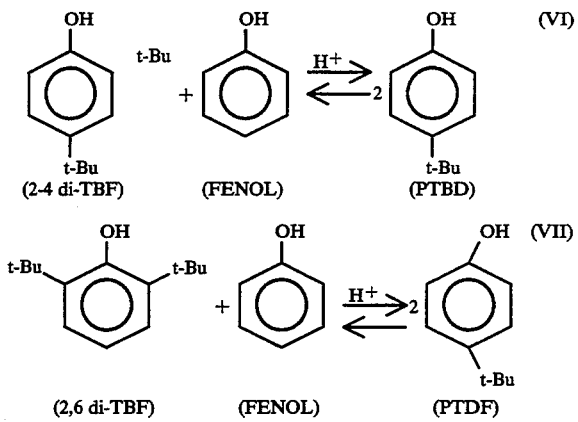

As it may be noted, the invention is quite versatile as to the aspect of working continuously or intermittently and also the type of bed, for instance, fixed, stirred or fluidized, depending from the type of catalyst used, for instance solid, in suspension, ion exchanging resin, etc.

Schedule 1 explains the process with alkylation and isomerization/translakylation steps in separate reactors and without the additional step of isomerization/translakylation. One starts form an alkylation reactor or reaction (1), where are loaded the reagents (2), i.e., phenol and alkyltert-butylphenilether. The reaction environment would then undergo a distillation step (3), and the lights from the reaction would escape from the top of the colums (4) and the product in the base would undergo an isomerization/translakylation step (5). The reaction environment would then undergo a neutralization step (6), with alkalis know to those skilled in the art, to be next submitted to another distillation (7). The product at the top, formed by the lights of the reaction, non reacted phenol and undesirable tert-butylphenols will be recycled for the first step of the process, i.e., alkylation. The product from the base would be routed to another distillation (B), i.e., through a rectification step, and coming out from the top of the column the desired tert-butylphenol (9) and at the base the heavies (1) of the process.

Schedule 2, is similar to schedule 1, only exemplifying alkylation and isomerization/translakylation steps taking place in the same device, in different steps and including the additional step of isomerization/translakylation.

Phenol (1) and alkyltert-butylether (2) are loaded into a reactor under stirring with simultaneous distillation (3). In a first step the alkylation reaction would take place and on a second step the isomerization/translakylation steps. The lights (4) would come out from the top and the product at the bottom would undergo a neutralization step (5). The neutralized product would then follow for a first distillation step (6) for the separation of lights/tert-butylphenol. The product from the bottom would be routed to another distillation step (7) or rectification step, which releases paratert-butylphenol (8) through the top of the column. The product from the top of (6) would undergo an additional isomerization/transalkylation step in this event containing a reactor under stirring (9) and a distillation column (10) which distillates the lights (12) simultaneously with the progress of reactions. The heavies from the process (11) may be burned or routed for an additional isomerization/transalkylation step.

The examples below explain the present invention, however, not limiting its scope or spirit.

EXAMPLE No. 1—Discontinuous Alkylation

In a reactor lined with stainless steel and 9 liters of useful volume, equipped with stirring device, thermometer and a small dam column (coluna de barragem) (diameter 50 mm and hight: 200 mm, filled with Raschig rings) are loaded: 4,5 kg (47,8 mol) of phenol, 3,16 kg (35,8 mol) of MTBE and 0.1 kg of sulphonic resin (AMBERLYST-15).

The mixture is stirred and heated at atmospheric pressure until 90° C. in 2 hours and this temperature is maintained for 2 hours.

At these conditions, 53% of phenol and 86% of MTBE are converted. The selectivity in t-butylphenols with relationship to phenols is $\geq 99\%$.

EXAMPLE NO. 2—Semi-continuous Alkylation

In the device described in example 1 are loaded 0.80 g of sulphonic resin (Amberlyst-15) and 4.00 kg (42.5 mol) of phenol.

The mixture is heated to 110° C. at atmospheric pressure.

3.75 kg (42.5 moles) of MTBE are added in a continuous fashion at a rate of 1.12 kg/h, and the temperature is kept at 110° C.

During the reaction, the distillation of 1.13 kg of lights containing 70% of methanol takes place.

There is also the formation of uncondensables (around 0.25 kg), which are burned.

At the end of the addition of MTBE (around 3.5 hs) one obtains conversions of 67% of phenol and 89% of MTBE and a selectivity in t-butylphenols of 99% with relation to phenol.

EXAMPLE 3—Continuous Alkylation

In a tubular lined reactor with 36 mm diameter and 2500 mm long, 2.51 of sulphonic resin (Amerlyte 125) are loaded.

The resin bed is flooded with melted phenol, and the reactor is kept heated through the circulation of the thermic fluid, through its lining.

The temperature and the technical fluid flow are regulated in order to keep 80° C. at the lower part of the reactor.

A mixture of phenol and MTBE (ratio 2.3:1) is fed in ascending flow at a 2.0 kg/h rate, temperature being kept a 80° C. and pressure at 5.0 kgf/cm$^2$.

In these conditions one obtains conversions of 38.5% of phenol and 92.3% of MTBE. The selectivity of t-butylphenols with relationship to phenol is $\geq 99\%$.

EXAMPLE 4—Intermitent Transalkylation of PTBA

Heating 95.9 g of phenol and 4.1 g of PTBA at 140° C. at atmospheric pressure, for 2 hours in the presence of 10 g of sulphonic resin Amberlyst-15 one obtains 2.2 g of PTBA and 1.6 g of anisole.

EXAMPLE 5—Intermitent Isomerization OTBF

| MTBE | 1.21% |
|---|---|
| MeOH | 3.03% |
| H2O | 1.21% |
| Anisole | 1.85% |

-continued

| | |
|---|---|
| Phenol | 79.73% |
| OTBF | 8.93% |
| PTBA | 3.99% |
| PTBF | 0.08% | at 120° C. and atmospheric pressure in the presence of sulphonic resin, Amberlyst-15 (30% w/w relative to the mixture), for 2 hours the conversion of OTBF into PTBF is 94.4%.

EXAMPLE 6—Intermitent Isomerization of OTBF/Transalkylation of PTBA

In a 2l. glass baloon, under stirring and a distillation column, is loaded a mixture of:

| | |
|---|---|
| MTBE | 12.1 g |
| MeOH | 30.3 g |
| H2O | 12.1 g |
| Anisole | 18.2 g |
| Phenol | 797.3 g |
| OTBF | 89.3 g |
| PTBA | 39.3 g |
| PTBF | 0.8 g |
| Amberlyst-15 resin | 350.0 g |

Temperature is regulated with an electric blanket at 135° C. and pressure is gradually reduced to 150 mmHg for the distillation of lights. At the end of three hours, are obtained 180.8 g of PTBF, with total conversion of PTBA and OTBF.

EXAMPLE 7—Continuous Isomerization of OTBF/Transalkylation of PTBA

In a 2.5l reactor, under stirring and with a distillation column with a 50 mm diameter and 2 m high filled with SULZER filling are loaded 1431 g of phenol, 270 g of PTBF and 447 g of sulphonic resin (Amberlyst-15).

The mixture in the reactor is heated to 135° C. at a pressure of 130 mmHg.

A mixture containing 82.2% of phenol, 1.5% of PTBA, 5.1% of OTBF and 1.1% of PTBF, 1.6% of anisole, 5.5% of methanol, 2.6% of water and 0.4% of others is continually fed at a rate of 2230 g/h.

Lights are continuously distilled at a rate of 250 g/h (lights being methanol, water, anisole and phenol) at a reflux rate of 10:1.

From the bottom are recovered at a rate of 1980 g/h the reaction mass which is isomerized/transalkylated.

At these conditions there is 92% transformation of OTBF and 86% of PTBA, both into PTBF.

EXAMPLE 8—Continuous Transalkylation of Dialkylphenols

In a 2 liter reactor under stirring with a distillation column 50 mm wide and 2 m high with Sulzer BX filling, is loaded 500 g of Amberlyst-15 resin.

At a rate of 2000 g/h is continuously loaded a mixture of:

| | |
|---|---|
| H2O | 0.70% |
| Anisole | 0.90% |
| Phenol | 81.20% |
| PTBF | 13.61% |
| di-TBF | 3.51% |

The reactor's temperature is kept at 120° C. and pressure is reduced for distilation of lights. At these conditions, 57% of di-TBF (di-tert-butylphenols) are transalkylated into PTBF.

EXAMPLE 9—Intermitent Isomerization/Transalkylation

In the same type of device described in example 1, 7.5 kg of a misture containing: 29.9% of phenol, 22,2% of OTBF, 25.3% of PTBF, 18.0% of di-TBF and 4.6% of lights, are submitted to a heating at 140° C. in the presence of 0.9 kg of sulphonic resin (Amberlyst-15).

At the end of two hours the reaction mass shows the following composition:

| | |
|---|---|
| Phenol | 23.4% |
| OTBF | 2.4% |
| PTBF | 65.6% |
| di-TBF | 4.4% |
| others | 4.2% |

EXAMPLE 10—Constinuous Isomerization/Transalkylation

In the same apparatus from example 3, the reactor is loaded with 500 ml of sulphonic resin (Amberlyst-15).

At a speed of 750 g/h is fed a mixture made of: 40.1% of phenol, 21.7% of OTBF and 14.1% of PTBF, 20.7% of di-TBF and 3.4% of others.

The resulting mass leaves the reactor, kept at 100° C. has the following composition:

| | |
|---|---|
| Phenol | 30.2% |
| OTBF | 2.3% |
| PTBF | 63.4% |
| di-TBF | 1.8% |
| others | 3.2% |

EXAMPLE 11—H2SO4 as Catalyst (Semi-continuous Alkylation+Isomerization/Transalkylation)

In the same type of apparatus used in example 1, arer loaded 4.00 kg (42.5 mol) of phenol and 41.2 g of sulphuric acid.

The mixture is heated at 110° C., under stirring and at atmospheric pressure.

2.83 kg (32.2 nol) of MTBE are continuously fed at a rate of 1.26 kg/h.

After approximately 30 minutes from the start of the addition of MTBE, starts the distillation of the methanol formed in the reaction.

After the addition of MTBE has taken place, the pressure is gradually reduced until it reaches 200 mmHg.

The temperature is then increased to 160° C. and this temperature is kept for 1.5 hours.

At the end of the reaction, one obtains 1.22 kg of distillate, containing around 81% of methanol.

During the reaction there is also the formation of non condensable gases (around 0.27 kg) which are burned.

The mass resulting from the reaction shows the following composition:

| | |
|---|---|
| Phenol | 25.8% |
| OTBF | 2.8% |
| PTBF | 63.8% |
| di-TBF | 6.0% |
| others | 1.6% |

EXAMPLE 12—Complete Process: Intermitent Reaction + Distillation with Reactor Under Continuous Isomerization/Translakylation In a reactor lined with stainless steel, with 20 liter capacity, under stirring and equiped with a small dam column (coluna de barragem) 50 mm wide and 200 mm high filled with Rashig rings, are loaded: 3942 g of new phenol, 2996 g of recycled phenol, 3968 of MTBE and 1300 g of sulphonic resin Amberlyst-15. The reactor is heated at a 90° C. temperature under atmospheric pressure for 2 hours and this temperature is kept for additional 2 hours.

Next the temperature is gradually increased (for 1 hour) until 140° C., distilling 1276 g of lights formed in the reaction, made of around 80% of methanol. This temperature is mantained for 2 additional hours for the isomerization of OTBF and translakylation of PTBA and di-TBF.

During reaction steps there is an escape of around 190 g of undensable gases which are burnt.

At the end of the reaction, the product obtained is transferred into an intermediate storage, and the resin which is used in the next operation is filtered, During the unloading of the mass obtained in the reaction, is neutralized passing through a column containing anionic resin in a fixed bed.

The total duration of the intermittent reaction cycle is 8 hours, taking into account 1 hour for transfers:

The mass obtained from the reaction contains:

| | |
|---|---|
| Phenol | 26.3% |
| PTBF | 63.3% |
| OTBF | 3.0% |
| PTBA | 1.4% |
| di-TBF | 2.0% |
| lights | 2.3% |
| heavies | 1.4% |

1180 g/h of the product obtained is distilled in a column 50 mm wide and 8 mm high with ordinated SULZER filling at a 40 mmHg pressure. The product from the bottom of the column (790.5 g/h) at a 150° C. is sent to the PTBF rectifying column.

The distilled product (389.5 g/h) is constituted by the lights, phenol and intermediate products feed a distillation column 50 mm wide and 2 m high and SULZER filling at a pressure of 150 mmHg, assembled over a isomerization/transalkylation reactor of 1 liter capacity, containing 70 g of sulphonic resin kept at 140° C.

From the top of this column are taken out 40.0 g/h of lights at a reflux rate adjusted in order to minimize the loss in phenol (RR: 10:1).

In the reactor, the molar excess of phenol and distillation favor the balance displacement of the translakylation reactions. To this reactor are also added 25.0 g/h of dialkylphenols resulting from the concentrate at the bottom of the PTBF rectifying column.

The product of the reaction (374.5 g/h) is the so called reclycled phenol.

The PTFB obtained (790.5 g/h) is rectified in a column with 50 mm diameter and 6 m high with SULZER filling at a 40 mmHg pressure and reflux rate of 2:1. The pure PTBF (750 g/h) thus obtained, has a polycarbonate degree quality, i.e., titer≧99.5% OTBF≦550 ppm, dialkylphenols≦550 ppm, phenols≦1000 ppm and melting temperature≧97.5° C.

The product from the bottom of the column at 170° C. containing dialkylphenols and other heavies (40.54 g/h) are concentrated in an evaporator to form a film, being the vapours condensed (25.0 g/h) and sent to the isomerization/translakylation reactor. The residue (15.5 g/h is sent to be burned.

The global yield of this process is 95% over phenol and 89% over MTBE.

EXAMPLE 13—Complete Continuos Process

In a tubular lined reactor with 36 mm diameter and 2500 mm long, containing 2,51 of sulphonic resin (Amberlyst-15), kept at 90° C. at atmospheric pressure, were continuously fed: 500 g/h of new phenol, 1736 recycled phenol and 495 g/h of MTBE. The mass resulting from the reaction which leaves the reactor passes through a degassing container, where 25 g/l of undecondensable gases are separated and directed to be burnt.

The product leaves the reactor after passing through the degassing container (2706 g/h), feeds a distillation column with 50 mm diameter and 2 m high filled with SULZER filling at a 150 mmHg pressure. 202 g/h of lights are distilled at a reflux rate of 10:1.

The product from the bottom (2504/h) kept at 140° C. feeds the isomerization/transalkylation reactor, containing a fixed bed with 4.01 of sulphonic resin (Amberlyst-15).

The mass obtained in the reaction is neutralized through the passage inside a column containing a fixed bed of anionic resin.

Next the neutralized mass of the reaction (2504 g/h) is distilled in a column 50 mm wide and 8 mm high with SULZER filling at a pressure of 40 mmHg. The distilled product (1736 g/h), made up of lights, phenol and intermediate products are recycled in the alkylation reactor.

The raw PTBF (768 g/h), taken from the bottom of this column at 150° C. is rectified in a column with 50 mm diameter and 6 m high with SULZER filling at 40 mmHg pressure at a reflux rate of 2:1.

The pure PTBF (750 g/h) thus obtained shows a polycarbonate degree quality, i.e., titer≧99.5%, OTBF≦500 ppm, dialkylphenols≦500 ppm, phenol≦1000 ppm and melting temperature≧97.5° C.

The residue (18 g/h) is recovered through the bottom of the column at 170° C. is sent to be burnt.

The global yield is 94% over phenol and 89% over MTBE.

It is claimed:
1. A process for obtaining tert-butylphenols, the process comprising the following steps:
 (a) alkylation in a bed reactor by reacting an alkyltert-butylether having an alkyl group containing from 1 to 6 carbon atoms with a phenol at a temperature ranging between about 60° C. and 130° C. and pressure ranging between atmospheric pressure and 5 kg/cm$^2$, in the presence of an acid catalyst, the molar ratio of alkyltert-butylether to phenol ranging between 0.1:1 and 2:1;
 (b) passing the product obtained in the alkylation step (a) through a distillation column, with temperature ranging between about −15° C. and 120° C. and pressure ranging between about 10 mmHg and 5 kg/cm$^2$;
 (c) isomerization/transalkylation of the product recovered at a bottom of the column in step (b) by routing said product to a fixed bed reactor, in the presence of a catalyst and with temperatures ranging from about 90° C. to 250° C. and pressure ranging between about 10 mmHg and 5 kg/cm²;

(d) neutralizing the product obtained from step (c) with alkalis at a temperature ranging between about 40° C. and 250° C. and pressure ranging between about atmospheric pressure and 5 kg/cm²;

(e) separation of lights/tert-butylphenol by distillation in a column at a temperature ranging between about 80° C. and 200° C. and pressure ranging between about 10 mmHg and 200 mmHg, the product from a top of the column being routed to the alkylation step (a) above; and (f) rectification of the product obtained at a bottom of the column from step (e), the product being sent for separation of the desired end product through distillation, tert-butylphenol being the product at the top of the column, said product being obtained at a temperature ranging from about 115° C. to 200° C. and a pressure of between about 10 mmHg and 200 mmHg.

2. A process as claimed in claim 1 further comprising passing the product obtained at the bottom of the rectification phase in step (f) through an evaporator to produce di-tert-butylphenols, said di-tert-butylphenols being recycled to alkylation step (a).

3. A process as claimed in claim 1 wherein the product from the top of the column in step (e) is subjected to an additional isomerization/transalkylation reaction of step (c) in the reactor with a distillation column for concurrent removal of lights from the mass of the reaction, at a temperature ranging between about 90° C. and 250° C. and pressure ranging between about 10 mmHg and 5 km/cm², and the product from the reactor is recycled to the alkylation step (a).

4. A process as claimed in claim 3 wherein the temperature is between about 100° C. and 160° C.

5. A process as claimed in claim 1 wherein the alkylation temperature ranges between about 70° C. and 110° C.

6. A process as claimed in claim 1 wherein the pressure during the alkylation step (a) is about atmospheric pressure.

7. A process as claimed in claim 1 wherein the temperature range in the reactor in the isomerization/transalkylation step (c) is between about 100° C. and 160° C.

8. A process as claimed in claim 1 wherein the temperature during the neutralization step (d) is between about 60° C. and 150° C.

9. A process as claimed in claim 2 wherein the di-tert-butylphenols emerging from the top of the evaporator are recycled to undergo a further isomerization/transalkylation step (a).

10. A process as claimed in claim 1 wherein the alkyl-tert-butylether is methyltert-butylether.

11. A process as claimed in claim 1 wherein the acid catalyst is of the protonated strong acid type.

12. A process as claimed in claim 1 wherein the acid catalyst is a Lewis acid.

13. A process as claimed in claim 1 wherein the steps are continuous.

14. A process as claimed in claim 1 wherein the steps are intermittent.

15. A process for obtaining tert-butylphenols, comprising:

(a) an alkylation and isomerization/transalkylation step in a reactor with simultaneous stirring and distillation in a column, wherein alkyltert-butylether having an alkyl group containing from 1 to 6 carbon atoms is reacted with a phenol, at a first phase temperature between about 60° C. and 130° C. and pressure between about atmospheric pressure and 5 kg/cm², the reaction being in the presence of an acid catalyst, the molar ratio of alkyl-tert-butylether to phenol being between 0.1:1 and 2:1, the temperature in a second phase being between about 90° C. and 250° C. and the pressure between about atmospheric pressure and 5 kg/cm²;

(b) neutralization of the product obtained from a bottom of the column in step (a) with alkalis and resins, at a temperature ranging between about 40° C. and 250° C. and pressure ranging between about atmospheric pressure and 5 kg/cm²;

(c) separation of lights/tert-butylphenol by distillation in a column at a temperature of between about 80° C. and 200° C., and a pressure ranging between 10 mmHg and about 200 mmHg, the product from the top of the distillation column being recycled to alkylation step (a);

(d) rectification by routing the product obtained at a bottom of the distillation column of step (c) to a separation phase for obtaining the desired end product through distillation, the tert-butylphenol being recovered from a top of the column, rectification taking place at a temperature ranging from about 115° C. to 200° C. and pressure of about 10 mmHg to 200 mmHg.

16. A process as claimed in claim 15 wherein the product obtained at the bottom of the distillation column in step (d) above is passed through an evaporator, from which is recovered the undesired di-tert-butylphenols which are recycled to alkylation step (a).

17. A process as claimed in claim 15 wherein the product recovered from a top of the column in step (c) is routed for an additional transalkylation/isomerization step in a reactor with a distillation column for the simultaneous removal of the lights of the reaction, at a temperature between about 90° C. and 250° C. and a pressure between about 10 mmHg and 5 kg/cm².

18. A process as claimed in claim 15 wherein the product recovered from the top of a column in step (c), the lights/tert-butylphenols, is routed for an additional transalkylation/isomerization step, wherein the distillation of lights occurs first and thereafter the additional isomerization/transalkylation step, at a temperature ranging between about 90° C. and 250° C. and pressure ranging between about 10 mmHg and 5 kg/cm², the product from the top of the column being recycled to the alkylation step.

19. A process as claimed in claim 15 wherein the temperature in step (a) ranges between about 60° C. and 110° C. in the first phase, and between about 100° C. and 160° C. in the second phase.

20. A process as claimed in claim 15 wherein the pressure in step (a) is substantially atmospheric pressure.

21. A process as claimed in claim 15 wherein the temperature in neutralization step (b) is between about 60° C. and 150° C.

22. A process as claimed in claim 16 wherein the ditert-butylphenols emerging from the top of the evaporator are recycled for an additional isomerization/transalkylation step.

23. A process as claimed in claim 15 wherein the alkyltert-butylether is methyltert-butylether.

24. A process as claimed in claim 17 wherein the temperature is between 100° C. and 160° C.

* * * * *